United States Patent
Nabors, Sr. et al.

(10) Patent No.: US 8,706,258 B2
(45) Date of Patent: Apr. 22, 2014

(54) METHOD AND APPARATUS FOR TREATING CANCER

(75) Inventors: William L. Nabors, Sr., Marietta, GA (US); Richard B. Ruse, Atlanta, GA (US); Scott J. Bohanan, Duluth, GA (US); E. David Crawford, Denver, CO (US)

(73) Assignee: MedAmp Electronics, LLC, Atlanta, GA (US)

( * ) Notice: Subject to any disclaimer, the term of this patent is extended or adjusted under 35 U.S.C. 154(b) by 0 days.

(21) Appl. No.: 13/569,574

(22) Filed: Aug. 8, 2012

(65) Prior Publication Data

US 2013/0041436 A1    Feb. 14, 2013

Related U.S. Application Data

(60) Provisional application No. 61/521,049, filed on Aug. 8, 2011, provisional application No. 61/521,235, filed on Aug. 8, 2011.

(51) Int. Cl.
    *A61F 7/00*    (2006.01)
    *A61B 18/14*   (2006.01)

(52) U.S. Cl.
    USPC .............. 607/99; 606/32; 606/34; 606/41

(58) Field of Classification Search
    USPC ......... 607/98–102, 113; 606/28–29, 39–41, 606/49–50
    See application file for complete search history.

(56) References Cited

U.S. PATENT DOCUMENTS

| | | | |
|---|---|---|---|
| 5,683,384 A | 11/1997 | Gough et al. | |
| 5,913,856 A * | 6/1999 | Chia et al. | 606/41 |
| 5,928,159 A | 7/1999 | Eggers et al. | |
| 6,106,524 A * | 8/2000 | Eggers et al. | 606/50 |
| 6,212,433 B1 | 4/2001 | Behl | |
| 6,909,917 B2 | 6/2005 | Woods et al. | |
| 7,890,183 B2 | 2/2011 | Palti et al. | |
| 8,019,414 B2 | 9/2011 | Palti | |
| 8,170,684 B2 | 5/2012 | Palti | |
| 8,175,698 B2 | 5/2012 | Palti et al. | |
| 8,216,219 B2 * | 7/2012 | Desinger et al. | 606/34 |
| 8,229,555 B2 | 7/2012 | Palti | |
| 8,244,345 B2 | 8/2012 | Palti | |
| 2002/0111615 A1 * | 8/2002 | Cosman et al. | 606/41 |
| 2003/0045871 A1 | 3/2003 | Jain et al. | |
| 2003/0069573 A1 * | 4/2003 | Kadhiresan et al. | 606/41 |
| 2003/0130711 A1 | 7/2003 | Pearson et al. | |
| 2003/0139790 A1 | 7/2003 | Ingle et al. | |

(Continued)

FOREIGN PATENT DOCUMENTS

WO    2008014465 A2    1/2008

*Primary Examiner* — Ronald Hupczey, Jr.
*Assistant Examiner* — Adam Avigan
(74) *Attorney, Agent, or Firm* — William H. Dippert; Eckert Seamans Cherin & ellott, LLC

(57) ABSTRACT

A method and apparatus for treating masses, such as prostate or breast cancer, or any other soft tissue cancerous or benign mass, employs a unique, three-dimensional software-controlled electronic amplifier array using arbitrary waveforms that dynamically and proportionally steer electrical currents by using two or more current vector paths, sequentially or simultaneously, through a mass containing electrically-conductive ionic solutions so as to obtain 100% thermal heating or hyperthermia through the mass, and destroying it with a minimally-invasive treatment which requires no radiation or chemotherapy which could be harmful to the patient.

17 Claims, 11 Drawing Sheets

(56) References Cited

U.S. PATENT DOCUMENTS

| | | |
|---|---|---|
| 2003/0195503 A1* | 10/2003 | Jain et al. .................. 606/41 |
| 2004/0267340 A1* | 12/2004 | Cioanta et al. ............ 607/105 |
| 2005/0165390 A1* | 7/2005 | Mauti et al. ................. 606/41 |
| 2007/0255269 A1* | 11/2007 | Shin ............................ 606/34 |
| 2009/0018533 A1 | 1/2009 | Perkins et al. |
| 2009/0024075 A1 | 1/2009 | Schroeppel et al. |
| 2009/0076502 A1 | 3/2009 | Azure et al. |
| 2010/0261994 A1* | 10/2010 | Davalos et al. ............ 600/411 |
| 2011/0130816 A1 | 6/2011 | Howard et al. |
| 2012/0220998 A1* | 8/2012 | Long et al. .................. 606/41 |
| 2012/0310230 A1* | 12/2012 | Willis ......................... 606/33 |

\* cited by examiner

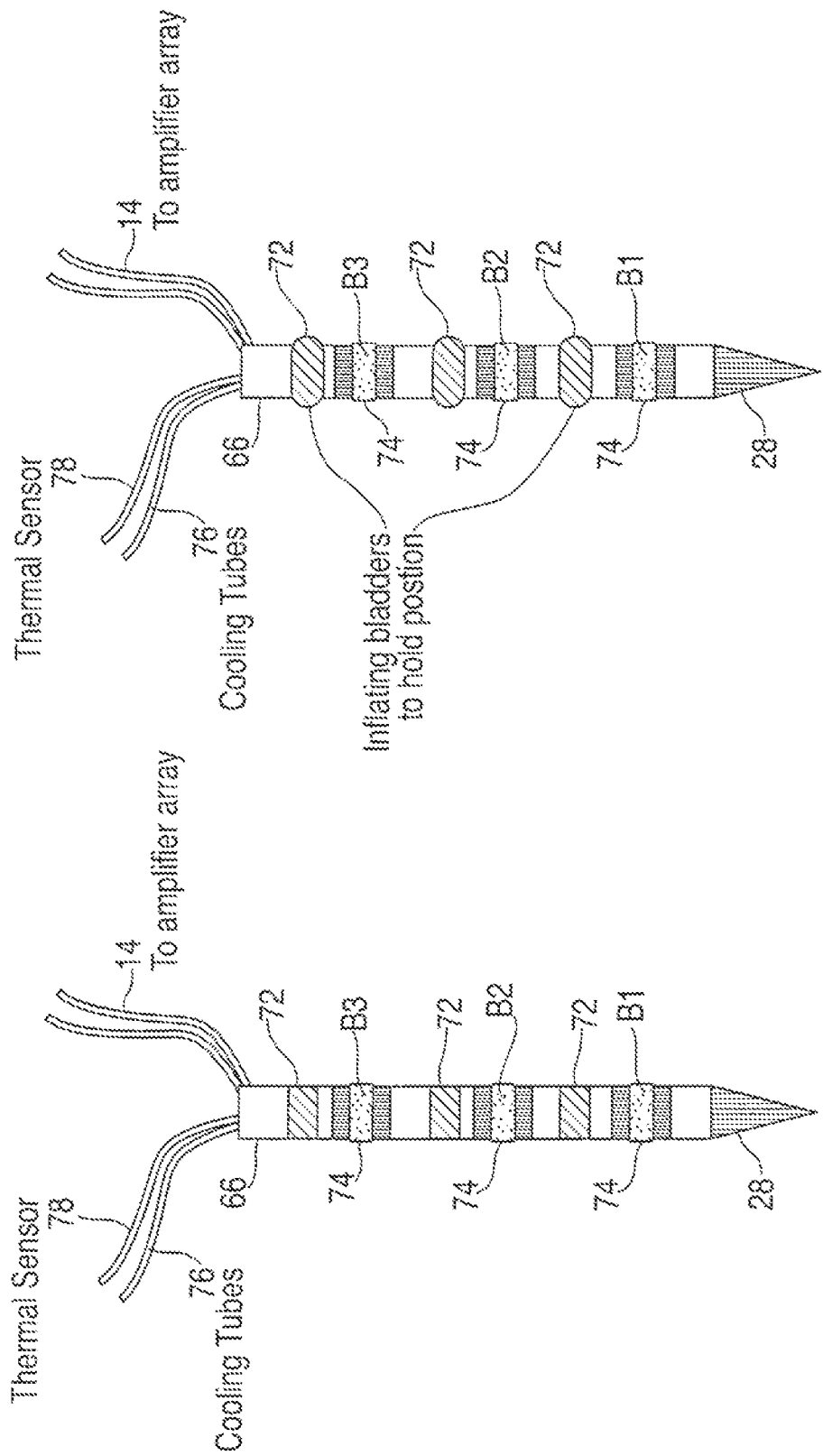

METHOD AND APPARATUS FOR TREATING CANCER

CROSS-REFERENCE TO RELATED APPLICATION

This application is based upon and claims the benefit of the filing dates of co-pending U.S. Provisional Patent Application Ser. No. 61/521,049, filed Aug. 8, 2011, and co-pending U.S. Provisional Patent Application Ser. No. 61/521,235, filed Aug. 8, 2011, both of which are incorporated herein by reference in their entirety.

FIELD OF THE INVENTION

This invention is directed to the treatment of masses, such as prostate or breast cancer, or any other soft tissue, malignant or benign cancerous mass, where standard surgery makes it difficult to remove the mass in its entirety due to proximity to other organs, vasculature, or other critical tissue. More directly, the cancerous mass is destroyed in situ, which may allow eradication of masses that may have previously been inoperable.

BACKGROUND OF THE INVENTION

According to the American Cancer Society, 7.6 million people died from cancer in 2007. This disease affects people of all ages, and treatment options currently include surgery, radiation therapy, immunotherapy, cryotheraphy, laser therapy, and chemotherapy. Surgery, alone or in conjunction with other treatments, is used in more than 9 out of 10 cases.

Surgery can involve partial or complete removal of an organ and/or the area affected by a cancerous tumor. However, in some cases, the tumor is inaccessible or has so completely invaded an area that this option, is not viable. In addition, accompanying therapies, such as radiation or chemotherapy, can cause serious or life-threatening side effects or affect other healthy tissue. Also, the number of treatments the patient can receive are limited.

OBJECTS OF THE INVENTION

It is an object of the invention to provide a method and apparatus for treating a malignant or benign cancerous mass.

It is also an object of the invention to provide a method and apparatus for treating prostate cancer or breast cancer.

It is a further object of the invention to provide a method and apparatus for treating a cancerous mass that may have been considered inoperable.

It is a yet further object of the invention to provide a method for treating a cancerous mass that comprises surrounding the cancerous mass with at least three shafts, each shaft having at least two electrode bands or contact points, and applying sufficient electrical current or energy in dynamically and proportionally steered current vectors to destroy cancer cells.

It is a yet further object of the invention to provide an apparatus comprising at least three electrode shafts, each electrode shaft having at least two electrode bands or contact points and being capable of applying sufficient electrical current or energy in dynamically and proportionally steered current vectors to destroy cancerous cells.

It is a yet further object of the invention to provide a method and apparatus for treating a cancerous mass wherein the electrical current applied has waveforms that are chosen by proprietary software to be particularly effective.

It is a further object of the invention to provide a method and apparatus for treating cancer where each electrode shaft comprising electrodes has a distal tip comprising a rigid dissolvable salt coating or compound or a functional equivalent, to eliminate tissue damage within a patient after the electrode shaft is inserted.

It is a yet further object of the invention to provide a method and apparatus wherein each electrode band or contact point on a shaft comprises a thermal sensor.

These and other objects of the invention will become more apparent from the description below taken in conjunction with the attached detailed drawings.

SUMMARY OF THE INVENTION

Applying an electrical direct current (DC) through an ionic mass or ionic solution produces heating or hyperthermia. Also, applying an electrical alternating current (AC) through an ionic mass or liquid solution produces heating or hyperthermia. The only difference between DC and AC currents applied through an ionic mass is that with DC current one electrode is an anode and the other electrode is a cathode. Chemical reactions occur at the two electrodes that take electron voltage, and current applied to the electrodes and the first electrode in the ionic mass converts the energy into ionic current through the mass or solution. At the second electrode the ionic current is converted back into electron current of the opposite polarity. Electron current can be conducted through a metal conductor such as a wire where ionic current cannot flow through a wire, only an ionic solution or ionic mass. When AC current is used, each of two electrodes where an AC voltage and current are applied causes each electrode to convert the electron current flow into an ionic current flow. However, when AC current is applied through an ionic media, each electrode becomes an anode and a cathode by changing functions, alternating back and forth at the frequency of the AC current. Thus, AC or DC current will produce heating through an ionic mass provided that an ionic solution exists in sufficient density for an ionic current to flow and generate heat.

According to the invention, a method and apparatus are provided for dynamically and proportionately steering or selecting two or more current vector paths, sequentially or simultaneously, for heating and destroying cancerous cells within a mass. Other traditional devices use a single current path or devices that deliver current across two or more current pathways. However, they cannot dynamically steer and proportionally induce hyperthermia by altering the voltage, current amplitude, and pulse-widths, or employ arbitrary waveforms through each pathway.

According to an aspect of the invention, an electrode system comprises three or more essentially non-conductive longitudinally extending members or shafts that will each comprise two or more, preferably three, electrode bands or contact points. Each electrode band or contact point is in electrical communication with an amplifier, and a thermal sensor is attached to each electrode band or contact point. Each thermal sensor is in electrical communication with a controller or processor. The shafts are designed with a very small insertion diameter and are tipped with a rigid dissolvable salt coating or compound, or a functionally equivalent coating, to protect tissue within a patient. These shafts are positioned strategically around and in close proximity to a mass to be treated.

According to another aspect of the invention, a method and apparatus use shafts with specifically designed electrodes that are electrically and mechanically manufactured to optimize the treatment for the specific cancerous mass and/or the organ, to be treated. The shafts may simply comprise electromechanical electrodes, or they may be designed to be inflatable with air or fluid, or to be dynamically cooled, or to allow for mechanical stability to hold position during the treatment.

According to another aspect of the invention, electronic circuitry waveforms are employed which include, but are not limited to, arbitrary waveforms of any form, amplitude or pulse-width (sine, square, triangle, curved, damped-sinusoidal positive or negative, with varying pulse width modulation) using direct current (DC) and/or alternating current (AC) and frequencies of voltage dependent upon the situation/mass and the treatment required. The waveform shapes are generated by a processor under software control interfaced with a computer. The energy is further amplified and delivered differentially between amplifiers without the use of a ground return.

According to another aspect of the invention, the electrodes electrically heat tissue in the mass, destroying the tissue. The electrodes are positioned around, but do not enter, the mass itself. A processor will vary the voltage amplitude, current intensity and pulse-width to heat and maintain thermal averaging within the entire targeted mass. This eliminates the possibility of cancer ceils breaking tree and migrating to other areas of the body during the surgical process. It also allows the mass to convert to scar tissue, which can be left in place, or removed at a later time. The current pulses are kept within the area defined by the shaft placement via dynamic and proportional current steering as commanded via the processor so that a minimum of healthy tissue is affected by the cancer treatment.

According to another aspect of the invention, an amplifier array, in conjunction with the processor, can focus energy in any area within the mass (to create a "hot zone"). This is done by proportionally varying the voltage amplitude and pulse-widths between electrodes to dynamically and proportionally shift, steer, or create a "hot zone" anywhere in the mass in three dimensions. The surgeon can focus on specific areas within the mass to ensure destruction of all cancerous cells. This supplies the surgeon with yet another tool to physically destroy all malignant or benign cells.

In another aspect of the invention, a processor will start the treatment protocol by slowly ramping the voltage and current up to a level, for example, in the milliampere range, where the surgeon can verify that all amplifiers are conducting current as specified to achieve the desired temperatures. The thermal sensors provide data for the processor so the software commands can make adjustments to the amplifier drive voltage amplitudes and pulse-widths. The goal is to uniformly elevate the mass to a temperature of from about 48° C. to about 50° C., for from about 5 to about 10 minutes or until all malignant or benign cells within the mass are destroyed.

The time to heal from this procedure should be from a few days to about two weeks or so, at which point MRI, CT, and/or ultrasound scans can be employed to analyze the area of interest and verify that the mass has been destroyed. In addition to the quick healing time, an advantage to this treatment is that unlimited additional treatments may be made to "touch tip" any cells that were missed during the initial treatment. Furthermore, no damaging radiation or chemotherapy would be required to affect the cure, and there would be no migration of cells due to surgical intrusion.

In another aspect of the invention, a processor is used to drive a preamplifier and amplifier which dynamically and proportionally steer current vectors between specially-designed electrodes on shafts inserted strategically around the mass in an infinite variety of waveforms which include, but are not limited to, arbitrary waveforms of any shape, amplitude or pulse-width using direct current (DC) and/or alternating current (AC) and frequencies of AC up to about 1 KHz of voltage, dependent upon the situation/mass and the treatment required. The surgeon can use the processor to vary the voltage amplitude, current intensity, and/or pulse-width and select any arbitrary waveform to heat and maintain thermal averaging throughout the entire targeted mass to an equal temperature sufficient to destroy the offending cells in situ. The energy can also be used to include a perimeter hyperthermia zone around the mass in three dimensions to ensure all microscopic cancerous cells are captured in the treatment.

In another aspect of the invention, a method is described to deliver monophasic and biphasic ascending or descending exponential, ramp or damped sinusoidal waveforms which are most efficient with respect to heating a cancerous or benign mass by using an amplifier array where any three or more amplifiers and their respective electrodes may be driven differentially as to draw current through selected current pathways or different angular perspectives within the cancerous mass. Also, any one amplifier may be driven differentially to any of the other amplifiers in the array sequentially and/or simultaneously using the same arbitrary waveform or any amplifier may be driven differentially to any of the other amplifiers sequentially using different arbitrary waveforms at different or equal voltage and current amplitudes. By use of this approach, many combinations of electrical current deliveries are possible and can be selected by the surgeon based upon individual patient requirements for tumor destruction within a three dimensional construct.

In another aspect of the invention, the amplifiers will process any waveform and voltage amplitude through the mass as directed and selected by the surgeon, such as ascending or descending exponential, ramp, damped sine, square, sine, triangle, saw tooth, etc. The voltage amplitude range shall be from about 0 to about +/−200 VDC.

In another aspect of the invention, a method of treating masses comprises dynamically and proportionally steering or selecting two or more current vector paths sequentially or simultaneously for ceil destruction.

In another aspect of a method of the invention, the method is carried out with differentially driven amplifiers, rather than a single current path or using the devices that deliver current and energy across two or more current pathways, but that cannot dynamically and proportionally alter the voltage and current amplitude through each pathway.

In another aspect of the invention, a method can treat masses in hard or soft tissues.

In another aspect of the invention, a method of treating masses comprises delivering biphasic ascending or descending exponential, ramp or damped sinusoidal waveforms which are most efficient with respect to the cell conduction by using an amplifier array where any two, three, or more amplifiers and their respective electrodes may be driven differentially and proportionally as to draw current through selected current pathways or different angular perspectives with the mass.

In another aspect of a method or apparatus of the invention, any one amplifier may be driven differentially to any of the other amplifiers sequentially and/or simultaneously using the same arbitrary waveform. Alternatively, any one amplifier may be driven differentially to any of the other amplifiers sequentially and/or simultaneously using individual and different arbitrary waveforms at different or equal voltage and current amplitudes.

In another aspect of a method of the invention, a positive pulse may use a square wave and a negative pulse may use a ramp waveform, or any waveform shape. This allows the plus and minus waveform shapes to be mixed and matched to achieve optimum treatment results.

In another aspect of a method of the invention, the surgeon can select pre-programmed and pre-defined software waveform protocols, wherein many combinations of current deliveries are possible based on individual patient requirements for destruction of cancer cells.

In another aspect of a method of the invention, the individual requirements are selected from the software protocol based on various medical criteria as defined by the surgeon.

In another aspect of a method or apparatus of the invention, waveform protocols are pre-programmed and pre-defined and are loaded into a processor memory for quick execution.

In another aspect of a method or apparatus of the invention, 100 or more protocols can be stored for a surgeon to select from the computer menu.

In another aspect of a method or apparatus of the invention, arbitrary waveforms can be delivered to multiple electrode configurations, and multiple sequential or simultaneous 3-dimensional current paths can be employed, In another aspect of a method or apparatus of the invention, the amplifiers will process any waveform through the mass directed by a surgeon such as ascending or descending exponential, damped sine, ramp, square, sine, triangle, ramp or saw tooth, in DC or AC positive or negative pulses.

In another aspect of a method or apparatus of the invention, monophasic or biphasic sequential or simultaneous current pulses are in the range of from about 0 ms to about 10 S positive and negative time periods, respectively.

In another aspect of the invention, an apparatus for destroying masses comprises means for dynamically and proportionally current steering or selecting two or more current vector paths sequentially or simultaneously through an amplifier and electrode delivery system for cell destruction.

In another aspect of the invention, the apparatus accomplishes its purpose by dynamic and proportional current steering rather than using traditional devices which destroy partial masses using single current path or devices that deliver energy across two or more current pathways, but that cannot dynamically and proportionally alter the voltage, current amplitude and current pulse-widths through each pathway.

In another aspect of an apparatus of the invention, any one amplifier may be driven differentially to any of the other amplifiers simultaneously using the same arbitrary waveform. Alternatively, any one amplifier may be driven differentially to any of the other amplifiers sequentially using individual or different arbitrary waveforms at different or equal voltage and current amplitudes, as well as varying pulse-widths to a achieve desired temperatures.

In another aspect of the invention, the possibility of cancerous or other cells from the mass breaking free and migrating to other areas of the body during the surgical process is eliminated. It also allows the mass to convert to scar tissue which can be left in place, or removed at a later time. The current pulses are kept within the radius of the electrode perimeters via dynamic and proportional current steering as commanded via the processor so that a minimum of healthy tissue is affected by the treatment.

In another aspect of the invention, electrode shafts will be designed such that the surgeon can easily see the difference between the platinum bands and the electrode shafts using existing ultrasound equipment. This facilitates the alignment of the electrodes relative to the mass of interest in three dimensions.

In another aspect of the invention, a method of treating a mass within a patient's body comprises dynamically and proportionally steering current vectors through the mass to heat the mass.

In another aspect of a method of the invention, three or more shafts comprising at least two electrodes on each shaft are positioned around the mass and voltages applied to the electrodes are varied to dynamically and proportionally steer current vectors through the mass.

In another aspect of a method of the invention, three shafts are used and each shaft has three electrode bands.

In another aspect of a method of the invention, the mass is heated sufficiently to destroy all of the cells within the mass.

In another aspect of a method of the invention, a processor-controlled electronic amplifier array generates signals to produce dynamically and proportionally steered current vectors under software control using a computer.

In another aspect of a method of the invention, the processor manages the voltage, current, pulse-widths, arbitrary waveforms and thermal data and makes adjustments to the amplifier drive voltage amplitudes.

In another aspect of a method of the invention, an ascending ramp will generate a rate of change slower than the leading edge of a square waveform.

In another aspect of a method of the invention, the current vectors create a hot zone within the mass.

In another aspect of a method of the invention, the current vectors uniformly elevate the mass to a temperature of from about 48° C. to about 50° C. until all malignant cells within the mass are destroyed.

In another aspect of a method of the invention, the mass is a cancerous or benign mass.

In another aspect of a method of the invention, the mass is prostate cancer or breast cancer.

In another aspect of the invention, a system for treating a mass within a patient's body comprises:
  three or more electrode shafts, each having at least two electrodes positioned along the shaft;
  a processor for generating instructive signals;
  an amplifier for receiving instructive signals from the processor and generating signals to the electrodes,
  wherein voltages of the electrodes are varied to dynamically and proportionally steer current vectors through the mass to heat the mass.

In another aspect of a system of the invention, the processor contains protocols to permit a surgeon to select a particular protocol.

In another aspect of a system of the invention, the system comprises three electrode shafts, each electrode shaft having two or more platinum bands or contact points.

In another aspect of a system of the invention, each electrode shaft had a small insertion diameter.

In another aspect of a system of the invention, each electrode has a thermal sensor.

In another aspect of a system of the invention, each electrode shaft has a distal tip with a coating or substrate comprising a dissolvable salt compound.

In another aspect of a system of the invention, each electrode shaft has one or more inflatable components that can be inflated to provide for mechanical stability while surrounding a cancerous or benign mass.

In another aspect of a system of the invention, the system which is suitable for treating masses which occur in the breast, liver, lungs, brain, pancreas, uterus, or ovaries.

In another aspect of a system of the invention, each electrode shaft comprises a cooling system to dynamically cool the electrode during treatment.

In another aspect of a system of the invention, the processor manages the voltage, current, pulse-widths, arbitrary waveforms and thermal data and makes adjustments to the amplifier drive voltage amplitudes.

In another aspect of a system of the invention, an ascending ramp will generate a rate of change slower than the leading edge of a square waveform.

In another aspect of a system of the invention, by using an amplifier array in conjunction with a processor, energy can be focused in any specific area within a mass by proportionally varying the voltage amplitude and pulse-widths between electrodes to dynamically shift or steer a hot zone anywhere in the mass in three dimensions, without moving the amplifier electrodes, to ensure destruction of all cancerous or malignant cells.

In another aspect of a system of the invention, the materials and construction of the electrode shafts and electrodes will be such that the difference between the electrodes and the electrode shafts will be readily apparent by use of conventional ultrasound equipment.

In another aspect of a method of the invention, a method of treating a mass within a patient's body comprises dynamically and proportionally steering current vectors around the perimeter of a mass to destroy the vasculature which feeds nutrients and blood supply to the mass.

In another aspect of a method of the invention, a method of treating a mass in a patient's body comprises the steps of:
 inserting two or more biopsy probes or needles into a patient to determine the extent of a mass, and
 dynamically and proportionally steering current, vectors through the mass to heat the mass.

In another aspect of a method of the invention, the biopsy probes or needles are removed before electrode shafts are inserted into the patient.

In another aspect of a method of the invention, the biopsy probes or needles are inserted into an organ.

In another aspect of a method of the invention, the organ is a prostate or a breast.

In another aspect of a method of the invention, biopsy probes or needles are capable of functioning as electrode shafts having two or more electrodes.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 7A and 7B are schematic representations in on-inflated and inflated states, respectively, of an inflatable electrode for treating cancerous or benign masses in human or mammal organs such as breast cancer or cancer in any other organ accessible by the system;

DETAILED DESCRIPTION OF THE DRAWINGS

Figure 1:
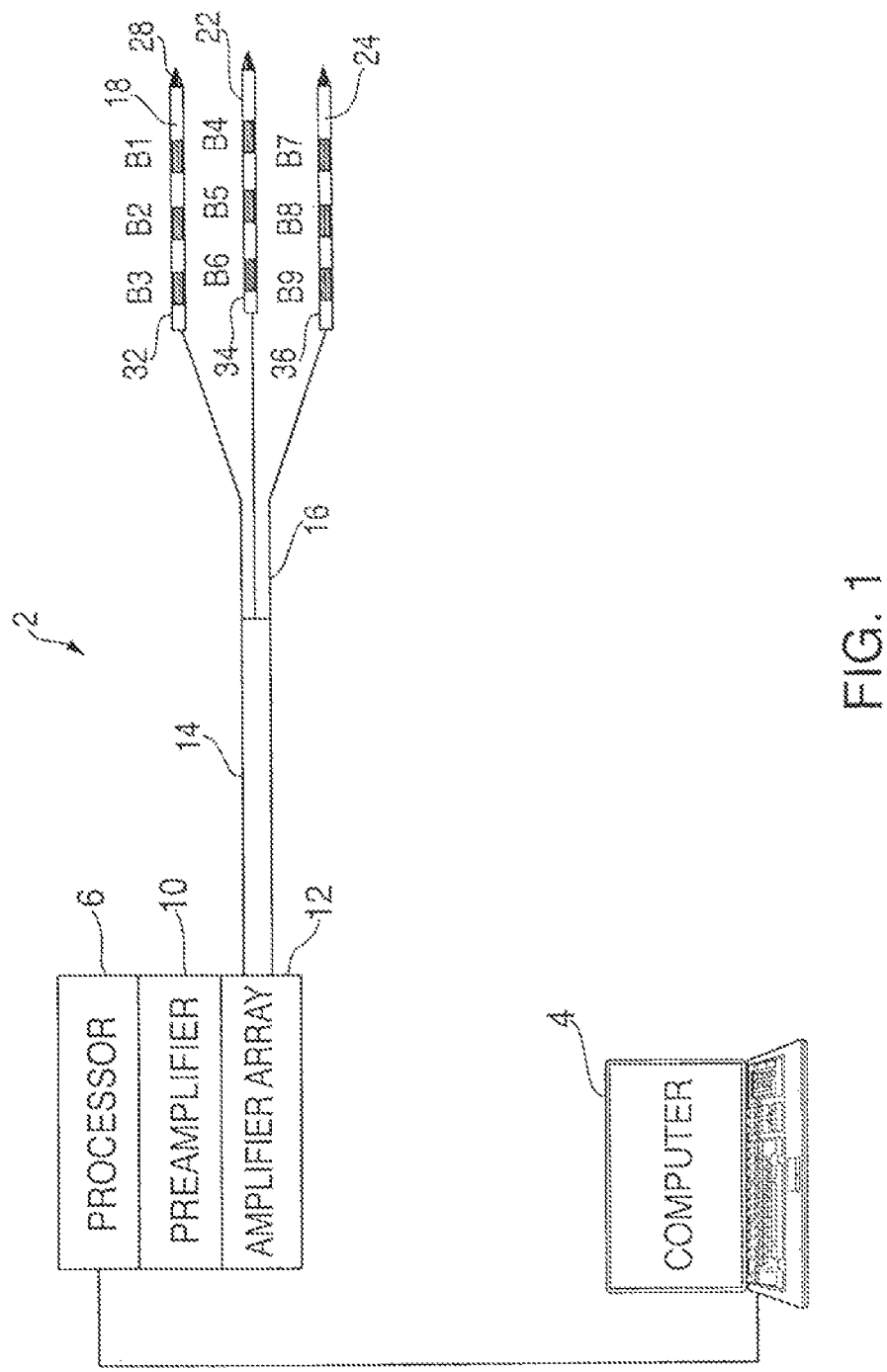
FIG. 1 is a schematic representation of one embodiment of a system useful according to the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs, As used herein, "directly coupled" means that two elements are directly In contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

By definition, electrolysis of water is the decomposition of water ($H_2O$) into oxygen ($O_2$) and hydrogen gas ($H_2$) due to an electric current being passed through the water. An electrolyte is any substance containing free ions that make the substance electrically conductive. The most typical electrolyte is an ionic solution, but molten electrolytes and solid electrolytes are also possible.

Commonly, electrolytes are solutions of acids, bases or salts. The human body is full of electrolyte solutions comprising, calcium, potassium, magnesium, etc., and all will conduct electricity.

If the above-described processes occur in pure water, $H^+$ cations will accumulate at the anode, and $OH^-$ anions will accumulate at the cathode. The negative hydroxyl ions that approach the anode mostly combine with the positive hydronium ions ($H_3O^{30}$) to form water. The positive hydronium ions that approach the negative cathode mostly combine with negative hydroxyl ions to form water. Relatively few hydronium (hydroxyl) ions reach the cathode (anode). This can cause a concentration over-potential at both electrodes.

This is applicable to the present invention. Dynamic and proportional current steering can be applied through an ionic solution or ionic mass. With regard to electrical currents, there are two basic conduction methods. First, electrons flow through conductive metals such as copper, silver, gold, steel, aluminum, etc. If alternating current (AC) is applied, the current flow will be positive to negative and negative to positive, alternating at the selected frequency between electrodes which become anodes and cathodes alternating respectively. With direct current (DC), through a conductive metal, electrons flow from negative to positive with the cathode being the negative and the anode being the positive. Current will only flow in one direction, and it is not alternating.

The second major category is electrical currents through an ionic-solution or ionic mass. If an electrical current is applied between two conductive electrodes while in distilled water or de-ionized water, little or no current will flow, whether AC or DC is applied. However, if one adds an ionic element or electrolyte solution into the distilled or de-ionized water, such as sodium, potassium, calcium, etc., or homogenizes them into a solid mass, they now become electrically conductive, but not in the same way as the electron flow described above.

For example, if two electrodes which are electrically conductive are placed in a salt-water solution, and a direct current and voltage are applied of sufficient amplitude, electron current will flow through the wires from the power source such as a battery or power supply to and from the electrodes. However, electrons cannot flow between the electrodes in the ionic solution. What occurs at each electrode in an ionic solution or mass is a chemical reaction between the electron carrying electrodes to and from the electrodes and the ionic solution at each electrode. One electrode is an anode which is positive, and one electrode is a cathode which is negative when using direct current (DC).

If one was to map and measure the current and energy field between the electrodes, it would become apparent quickly that there is a current density which is represented in an elliptical shape between the two electrodes. Within the ellipse, the current density will be most intense in a straight line between electrodes positive and negative in the solution or mass, that is, basically, the path of least resistance.

Medically, if an electrolyte such as a salt as added into pure water, the result is an ionic solution. When electrical energy is applied between two electrodes, it is electrons that are flowing, but only to the point where it is converted into a chemical reaction at the interface between the electrodes and the ionic solution or ionic mass where the energy is converted into ionic current.

An important characteristic of the invention described and claimed herein is that heat is generated between any two or more electrodes when electrical currents are applied. The challenge is to control the current vectors or paths to create heating or hyperthermia in the desired areas sufficient to destroy cancer cells. The preferred control percentage in terms of the cancerous mass would be 100% coverage.

To achieve a 100% heating or hyperthermia successfully within a cancerous or benign mass one must dynamically and proportionally steer currents between several electrodes in three dimensions to obtain the desired zones and coverage of hyperthermia. To dynamically and proportionally steer electrical currents through an ionic mass, one must add at least a third electrode and perhaps several electrodes to achieve the control required to destroy cancer cells and masses within the 3D confines of a human or mammal's organs. For example, if three electrodes 1, 2, 3 are equally spaced in a glass container 120° apart, and a direct, current and voltage of +100V to is applied to electrode 1 and −100V is applied to each of the other two electrodes 2 and 3, the result, will be an elliptical pattern of current between not only electrodes 1 and 2, but also between electrodes 1 and 3. There will be an Ionic current flow in each of two directions with equal current densities. Both paths will generate heat or hyperthermia.

Further, if both voltages are of equal potential, there will be two elliptical patterns in two different directions. If it is desired to steer the current between electrodes 1 and 2 and electrodes 1 and 3, one would lower the voltage on electrode 2 and increase the voltage on electrode 3. The current density between electrodes 1 and 2 will not be equal to the current density between electrodes 1 and 3. The current density will shift such that a lower current density will be present between electrodes 1 and 2, and a higher current density will be present between electrodes 1 and 3. Also, importantly, as the voltage rises between selected electrodes, the impedance or resistance within the ionic mass will drop and increased current is a result. Thus, by raising and lowering the voltage output between three or more amplifiers, the currents between electrodes will rise and fall as commanded by the processor, and, as a result, increased or decreased hearing will occur in the areas selected for treatment. Increased current results in increased heating.

If one wishes to dynamically and proportionally steer current through an ionic solution in 360°, all three electrodes will be used. This dynamic and proportional steering is accomplished by varying the voltages and currents between all three electrodes at varying voltages and current intensities and rates of change among all three electrodes as commanded through the amplifier array via the processor and computer commands. Now, instead of discrete elliptical current patterns and densities within the construct of this 360° ionic solution, there will be a homogenized and an equal hyperthermia pattern or a focused hyperthermia pattern may be created via the amplifier array and its computer-controlled commands. Not only can the hyperthermia patterns be radial, they may also be vertical or at any angular perspective desired to produce the desired hyperthermia within a 3D domain.

The rate of change or time it takes to increase or decrease the current density between electrodes 1 and 2 while transitioning to a higher or lower current density between electrodes 1 and 3 is a function of the rates of change in terms of time with respect to the rate of change of voltage and current it determines how fast the steering occurs. This is where having the capability to deliver arbitrary waveforms is significant. An ascending ramp will generate a rate of change slower than the fast leading edge of a square waveform.

If you have three amplifiers driven dynamically and proportionally using alternating or direct current, one can vary the amplitude of the voltage between electrodes 1 and 2 and electrodes 1 and 3 in a proportional fashion to lower the voltage between electrodes 1 and 2 while simultaneously raising the voltage between 1 and 3. As a result, the elliptical patterns become blended or homogeneous within the ionic solution or mass of interest and dynamic, proportional steering will occur.

If this is taken a few steps further, consider using three platinum band electrodes per electrode shaft in the same 120° scenario, with a volume of salt water, a depth, a diameter, and electrolyte ionic solution. With use of processor commands and a computer, arbitrary waveforms can be delivered with nine definitive electrode bands with a vertical span, circumference, or radius and depth. We now have the ability to control what is known as six degrees of freedom, including pitch, yaw, and roll. If these simple principles are applied using complex circuitry and software commands, and it is now possible to have 72 vectors of energy in the form of an ionic current flowing through a mass in three dimensions. In a more granular system, there may be 12 or more active electrode bands or 132 or more vectors of energy, all of which can be energized in all vectors point-to-point but they can also all be steered dynamically and proportionally by raising and lowering voltage and current amplitudes between all of the electrodes as commanded by the software and processor. There are two modes of operation: the system can be programmed to uniformly heat the solution or mass within the confines of the electrode amplifier array, or a focal "hot zone" or zone of heat that is more intense collectively than a generalized heated area can be produced. An analogy would be a magnifying glass in the sun. You can focus it on a piece of paper and the paper will burn. But if you take three magnifying glasses and focus them on the same point, you will get considerably more energy focused on the one point. If you want to move that optically heated point to a different location, you would simply tilt the lenses slightly in unison, to move the "hot zone."

The same thing is true with dynamically and proportionally steering current through an ionic mass. You can focus the energies of all nine or more electrodes at a targeted position, or you can steer currents in such a fashion as to raise and lower the temperature at will, or one may wish to induce thermal averaging and hold a specific temperature until the mass of interest is destroyed. Software commands the processor, which commands the preamplifier, which commands the amplifiers which deliver the voltage and current in sufficient energy levels between the electrodes as to create heat or induce hyperthermia, a byproduct of drawing current through an ionic solution or mass.

The ability to control energy in the form of heat, which is a byproduct of drawing voltage and current between several electrodes using software commands through amplifiers which supply a proportional ability to raise and lower voltage, allows the surgeon to heat any area of a mass without relocating the electrode shafts, the use of radiation or chemotherapy for the treatment of a cancerous or benign masses.

FIG. 1 is a schematic overview illustrating an oncology treatment system according to the present system. A system 2 comprises a computer 4 such as a laptop that provides the software waveforms and intelligent commands that direct a processor 6 which further processes commands from computer 4 to define and deliver the appropriate waveforms. Such waveforms include voltage amplitude, arbitrary waveforms, peak currents and other electrical attributes which are then converted within processor 6 from digital to analog signals. The analog signals are then delivered to a preamplifier 10 which provides a small voltage gain in amplitude so that the waveforms selected for treatment can be distributed and delivered into an amplifier 12, which then provides voltage and current amplification at much higher levels. That allows for voltage and current waveforms to be delivered through the proximal end of a common multi-conductor cable 14, which is of a sufficient length to reach from an equipment rack (not shown) to a patient (not shown). Computer 4 contains a user friendly menu so the surgeon may select which protocol be or she needs to destroy cancerous masses.

Cable 14 has a distal end 16 that is electrically connected to the proximal ends 32, 34, 36 of three cylindrical electrode shafts 18, 22, 24. Each electrode shaft 18, 22, 24 has at least three platinum electrode bands, identified here as bands B1 to B9. Each electrode shaft 18, 22, 24 has at its distal end a rigid dissolvable salt coating or substrate 28, to aid the surgeon with insertion into the patient. Such coating or substrate 28 will comprise a physiologically acceptable salt such as sodium chloride, potassium chloride, calcium chloride, or a functional equivalent. The coating or substrate 28 will partially or wholly dissolve during use, that is, after insertion into a patient's body.

At least the external surface of each electrode shaft 18,22, 24, if not the entire shaft, comprises a rigid or substantially rigid non-conductive, sterilizable, and physiologically and medically acceptable material such as a polyethylene, polycarbonate, or polyurethane polymer or copolymer. The size of electrode shafts 18, 22, 24 can vary according to intended use and/or the size of the mass to be treated. For example, electrode shafts 18, 22, 24 could be from about 10 cm to about 40 cm, preferably from about 15 cm to about 30 cm, in length and from about 0.9 mm to about 5 mm, preferably from about 1 mm to about 2.5 mm, in diameter. Electrode bands B1 to B9 are spaced from about 2 cm. to about 4 cm, preferably from about 2.5 to about 3.5 cm, apart with a width of from about 0.5 cm to about 5 cm, preferably from about 1 cm to about 4 cm.

Figure 2:
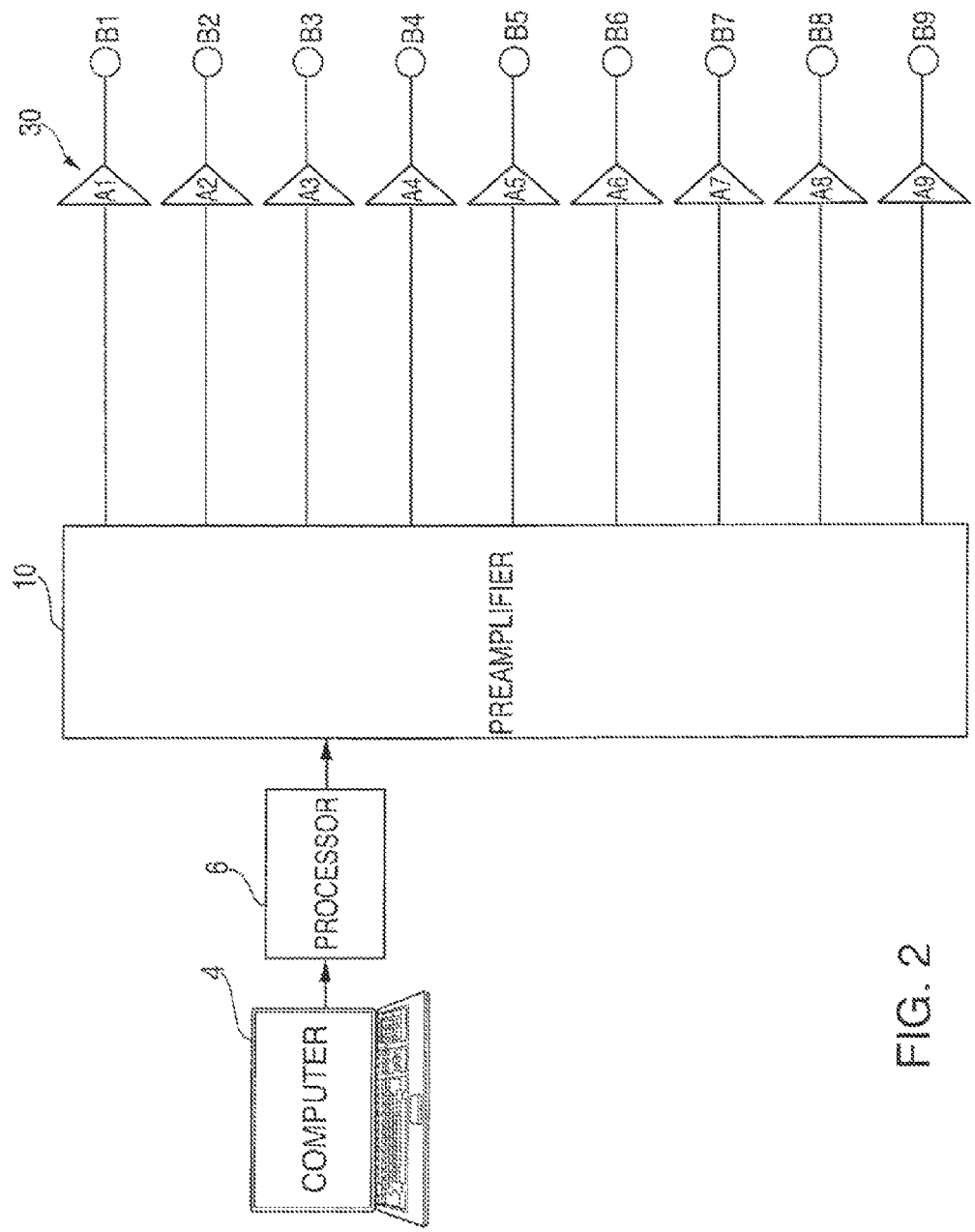
FIG. 2 is a detailed schematic representation of an aspect of a system according to the invention.

FIG. 2 is a detailed illustration of the system 2 shown in FIG. 1 where amplifier 12 from FIG. 1 comprises an array 30 of nine amplifiers A1 to A9, based upon three electrode shafts having three platinum electrode bands each, which amplifiers A1 to A9 amplify the signals into electrode shafts 18, 22, 24 and corresponding electrode bands B1-B9. If the three electrode shafts each had four electrode bands, there would be twelve amplifiers A1 to A12. Three or four electrode bands on each shaft are consistent with 9 to 12 amplifiers, although nine amplifiers is the optimal and typical system.

As illustrated, computer 4 sends digital signals to processor 6 and then into preamplifier 10, which distributes signals from processor 6 into as many preamplifier 10 output signals as are required for proper treatment of a malignant or benign mass 40.

The processor interprets the commands received from the computer and generates arbitrary waveforms of any shape, amplitude and pulse widths which are required to drive the amplifier array. Also, the processor converts the digital waveform information into analog waveform signals using a digital to analog converter. The analog waveform is amplified by the preamplifier. The preamplifier also serves as an electronic platform to mix and blend waveform signals prior to sending them onto the power amplifiers which make up the amplifier array as well as for thermal regulation and monitoring the current in each amplifier that makes up the array used for treatment.

Preamplifier 10 is required for two basic functions: First, it takes very small voltage signals and amplifies them to a level where a power amplifier array can be driven to the appropriate voltages and currents which are required to treat the cancerous or benign masses of interest. And second, the preamplifier circuitry also serves as a platform for receiving the thermal feedback and current data in "real time" and communicates with the processor so the software may make minor adjustments to raise and lower voltage amplitudes which affect current levels and thus affect thermal control within and around the mass of interest. Overall system feedback is important to affect the most successful medical outcome and for reasons of safety. The preamplifier in concert with the processor monitors all circuit functions so in the event of a component failure or power failure the system would shut itself down so as not to harm the patient being treated. Another aspect of this safety circuitry is it has the capability to run diagnostics on the amplifier array and make smart adjustments as required during therapy.

Amplifier array 30 comprises 9 to 12 or more amplifiers which are all identical in terms of circuit architecture. They are designed to deliver any voltage and current required to successfully treat cancerous or benign masses using voltages from about zero to +/−200V AC or DC. The voltage and current will be varied to achieve thermal averaging or a focused thermal zone of hypothermia as an effective treatment system for cancer in a patient. The amplifier array can be configured via software commands to operate in both constant voltage or constant current modes. Ultimately, having total control over heating the cancer or benign masses of interest in three dimensions make this a useful tool for cancer surgeons to increase cure rates among cancer patients.

The figures herein represent an exemplary depiction of three electrode shafts with three platinum electrode bands for delivering electrical currents in a prostate gland within a construct of three dimensions for the purpose of creating hyperthermia to destroy a cancerous or benign mass. It will be appreciated by those skilled in the art that there can be more than three electrode shafts, that each electrode shaft can have at least two, and perhaps as many as 4 to 8 or more electrode bands or contact points, and that each electrode shaft may not have the same number of electrode bands or contact points as another shaft. Further, while a platinum electrode band or contact point is preferred, other conductive materials, preferably radiopaque, such as nitinol or stainless steel, may be used.

Figure 3:
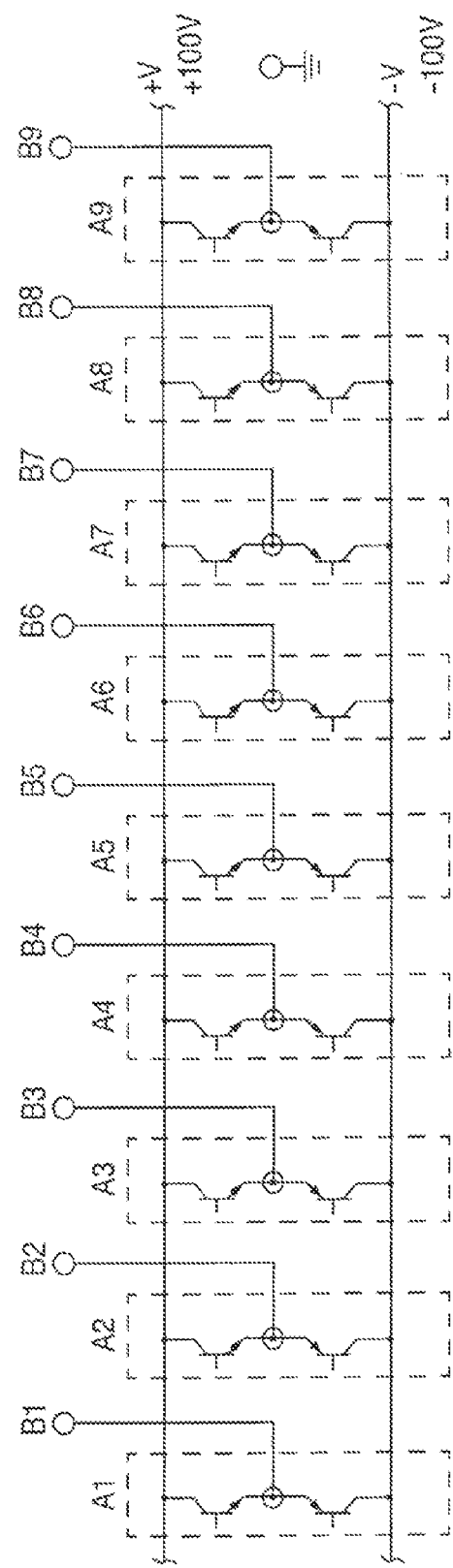
FIG. 3 represents a partial schematic of a differential amplifier array useful according to the invention.

FIG. 3 is a schematic illustration of the design architecture of a typical power amplifier array 30 comprising amplifiers A1-A9 in exemplary fashion. Each amplifier in array 30 differentially drives a signal into one of three electrode shafts 18, 22, 24 containing nine platinum electrode bands B1-B9. Amplifier array 30 is capable of delivering voltages and currents into electrode shafts 18, 22, 24 containing platinum electrode bands B1-B9 with an approximate voltage output of +/−100V AC or DC, which, when differentially driven, produces from about 0 to +/−200V. This proportional voltage and current delivery system allows for precise treatment options for the desired outcome as commanded by the surgeon via the computer 4, processor 6, preamplifier 10, and amplifier array 30.

Figure 4:
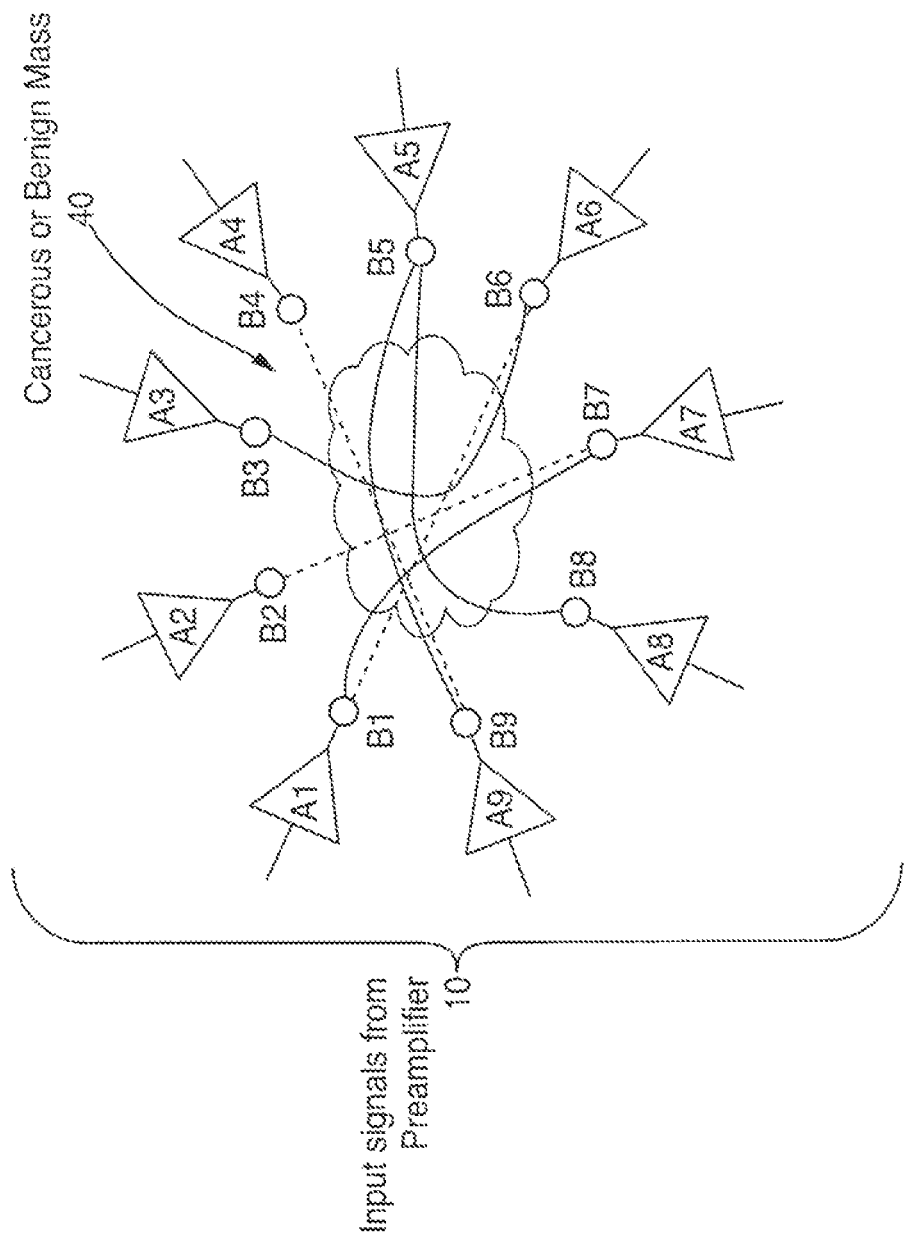
FIG. 4 is a schematic representation of one example of dynamic and proportional current steering according to the invention.

FIG. 4 is a schematic representation of an exemplary application of the amplifiers A1-A9 of array 30 in addition to electrode shafts 18, 22, 24 and their corresponding platinum electrode bands B1-B9, all delivering energy to and through a cancerous or benign mass 40. As depicted, voltage and current vectors may be delivered in straight lines or may be dynamically and proportionally steered as commanded by the surgeon via the computer 4, processor 6, preamplifier 10, and array 30 of amplifiers A1-A9.

Figure 5:
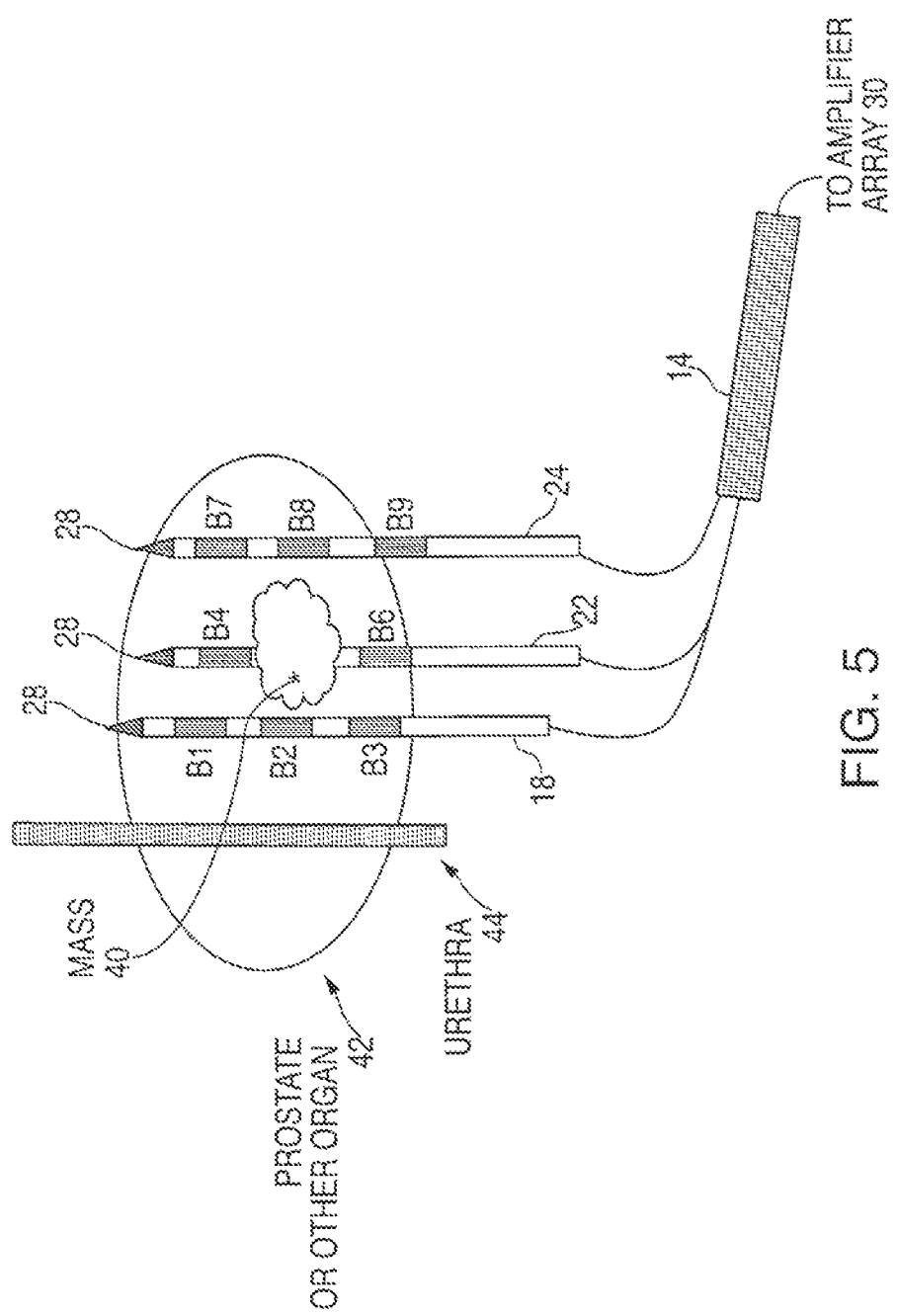
FIG. 5 is a schematic representation of use of a system according to the invention in treating a mass in a patient's prostate.

FIG. 5 illustrates an exemplary application for the treatment of a mass 40 within the construct of a prostate gland 42 or any other organ in a male patient or any organ in a female patient. A urethra 44 is depicted as it traverses prostate gland 42 for reference. Electrode shafts 18, 22, 24 are inserted into a patient, deep into the prostate gland, for the purpose of aligning the electrode shafts 18, 22, 24. Corresponding platinum electrode bands B1-B9 receive signals from cable 14 and amplifiers A1-A9 so as to surround cancerous or benign mass 40 of interest in a 3-dimensional (3D) construct. Electrode shafts 18, 22, 24 are designed in such a way so as to contrast on ultrasound video to discriminate between the platinum electrode bands B1-B9 and the non-conductive, shaft portion of electrode shafts 18, 22, 24. This aids the surgeon with the appropriate placement of the electrodes.

Figure 6A:
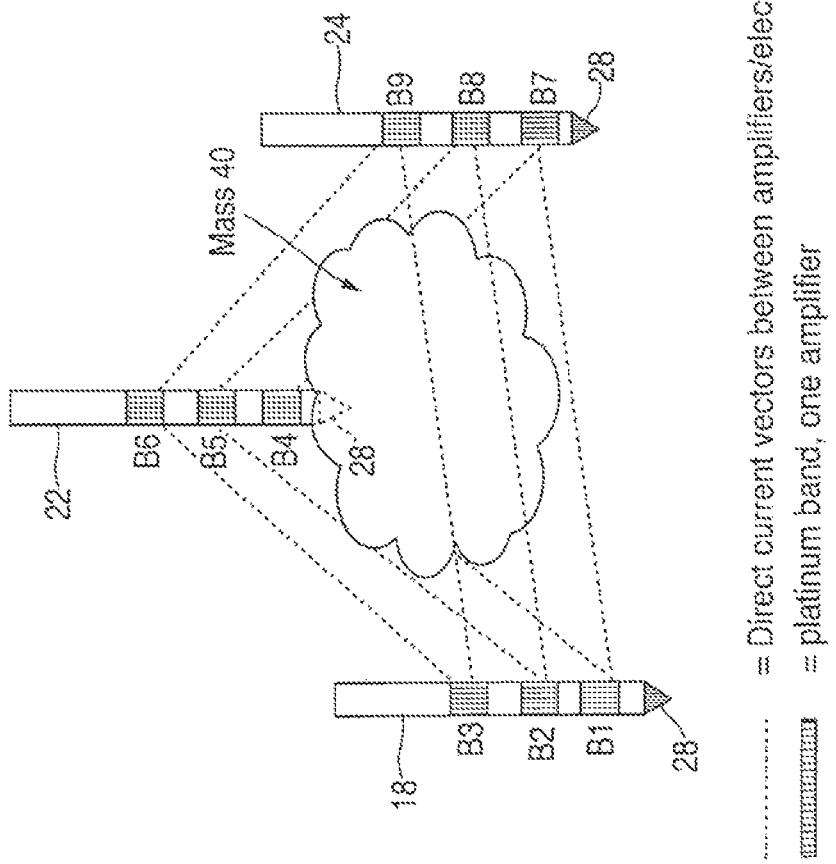
FIG. 6A is a representation of a traditional electrical current delivery between a plurality of electrodes that do not dynamically or proportionally steer electrical currents.

FIG. 6A is a schematic representation illustrating an exemplary two-dimensional system using electrode shafts 18, 22, 24 and their corresponding platinum electrode bands B1-B9, where voltages and currents are not dynamically or proportionally steered, through the cancerous or benign mass 40; rather, straight, point-to-point vectors will be generated. The nine platinum electrode bands B1-B9 are capable of producing up to 72 vectors; however, using this two-dimensional system, much of mass 40 cannot be subjected to heating or hyperthermia. Therefore, many of the cells contained within mass 40 will not be destroyed, providing an ineffective treatment.

Figure 6B:
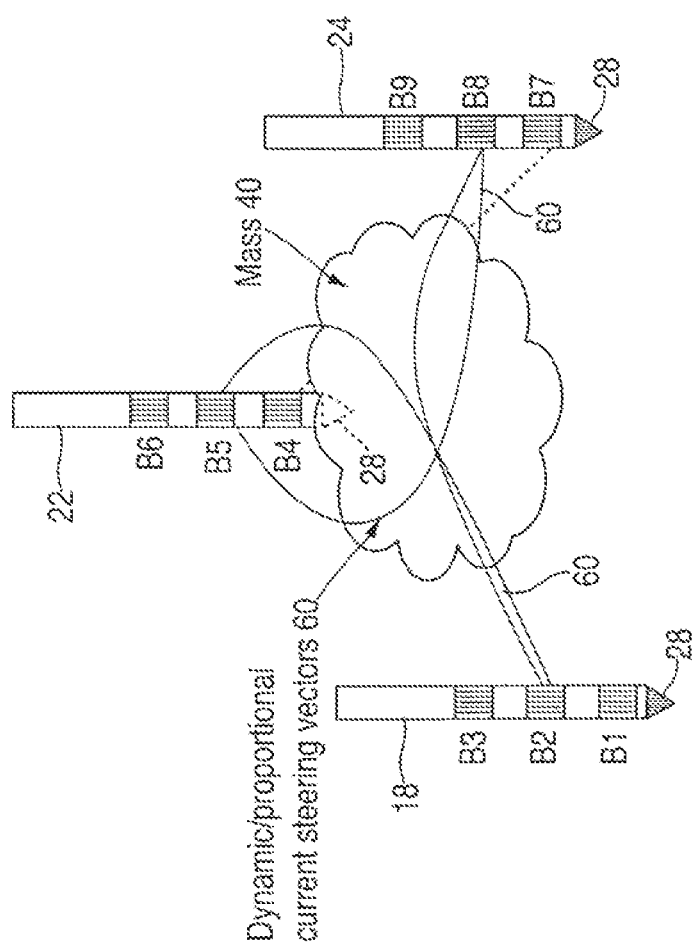
FIG. 6B is a representation of an example of electrical current delivery between a plurality of electrodes that dynamically and/or proportionally steer electrical currents in three dimensions for the purpose of creating hyperthermia in a mass with 100% coverage and no zones of unwanted cells missed by the treatment.

FIG. 6B is a schematic representation illustrating an exemplary three-dimensional system using electrode shafts 18, 22, 24 and their corresponding platinum electrode bands B1-B9, where voltages and currents are dynamically and/or proportionally steered as vectors 60 through the cancerous or benign mass 40. The nine platinum electrode bands B1-B9 are capable of producing up to 72 vectors 60 using this three-dimensional system. Since the voltages and currents are dynamically and/or proportionally steered through mass 40, 100% of mass 40 of interest can now be subjected to heating or hyperthermia either in a thermal averaging method or by proportionally commanding electrode shafts 18, 22, 24 so as to surround mass 40 of interest in a three-dimensional (3D) construct. Another benefit of using the software-commanded system is the ability to create and move an elevated zone of hyperthermia through mass 40 by applying the principle of delivering energy in six degrees of freedom, which represents three-dimensional heating of mass 40. Therefore, the cells contained within mass 40 will be destroyed, providing an effective treatment. An additional or optional aspect or benefit of using the three-dimensional hyperthermia treatment system with dynamic and proportional steering of current vectors is the ability to surround or "fence" the perimeter of a mass 40 with heat three-dimensionally to destroy the vasculature which feeds nutrients and blood supply to mass 40.

Figure 6C:
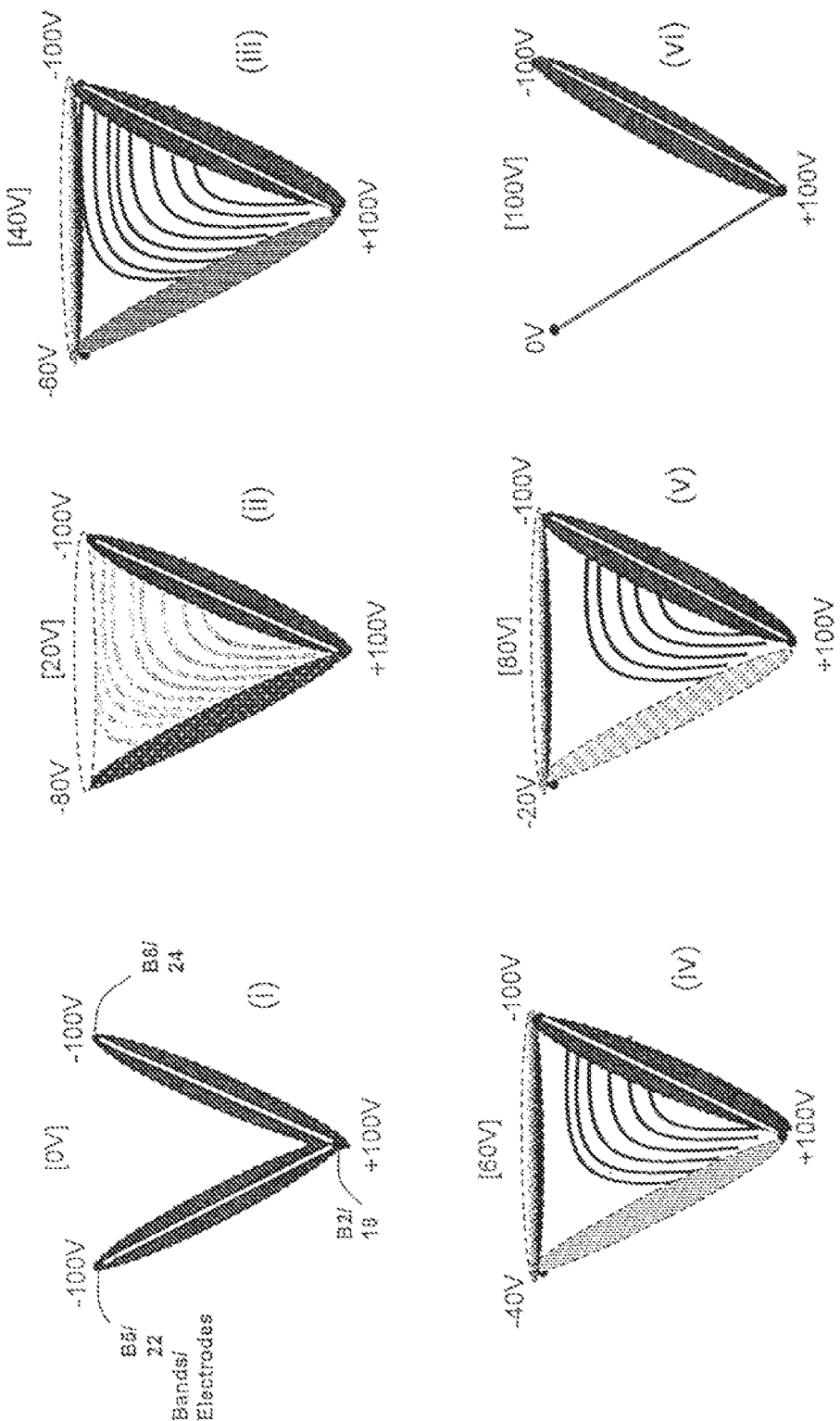
FIGS. 6C(i) to 6C(vi) are schematic representations of dynamic and proportional steering of current among three electrodes.

FIGS. 6C(i) to 6C(vi) are schematic cross-sections of an exemplary current steering pattern among electrode bands B2, B5, and B8 on electrode shafts 18, 22, and 24, respectively. As the voltage is commanded to be lowered on B5 by processor 4, there is a progressive shift in current flow as depicted in FIG. 6C(ii). The current between B2 and B5 begins to decrease, and because there is now a difference in voltage between B5 and B8, a current begins to flow between B5 and B8. As the voltage continues to decrease between B2 and B5, the current is proportionally steered through the ionic mass toward B8 as depicted in FIG. 6C(iii). The change in current flow in terms of time or rates of change is a function of the commands received from processor 4. If one applies this principle of operation to all nine electrode hands, a true 3-dimensional cancerous or benign mass may be heated equally or a focused zone of heat may be generated and moved within the mass via the processor commands. The current densities are shown with the darker areas having the higher current densities and the lighter shades have lesser current densities. Thus, voltage and current through an ionic mass generate heat or hyperthermia as follows: Increasing voltage=increasing current=decreasing impedance=increasing heat. Therefore, dynamic and proportional current steering occurs when voltages are raise and/or lowered between electrodes within an ionic solution or ionic mass.

FIGS. 7A and 7B are schematic representations of an electrode shaft 66 which would be ideal for treating masses which occur in the breast or organs such as the liver, lungs, brain, pancreas, kidney, uterus, or ovaries or other masses. In FIG. 7A, electrode shaft 66 has platinum electrode bands B1-B3 and deflated, but inflatable, flexible hands or pneumatic bladders 72. In addition, electrode shaft 66 has dissolvable rings of salt 74 around platinum electrode bands B1-B3 to increase and enhance electrical conductivity. In addition, wires 14 to the amplifier array 30, a cooling tube 76 and a thermal sensor 78 monitor the temperature of electrode shaft 66 during treatment.

A dissolving salt tip 28 is designed to enable easy insertion into an area of interest and to minimize or protect against tissue damage after insertion.

In FIG. 7B, the pneumatic bladders 72 on electrode shaft 66 have been inflated to mechanically stabilize electrode shaft 66 in the tissue surrounding a mass. After the electronic procedure is complete, pneumatic bladders 72 are deflated and electrode shaft 66 is removed from the patient.

Figure 8:
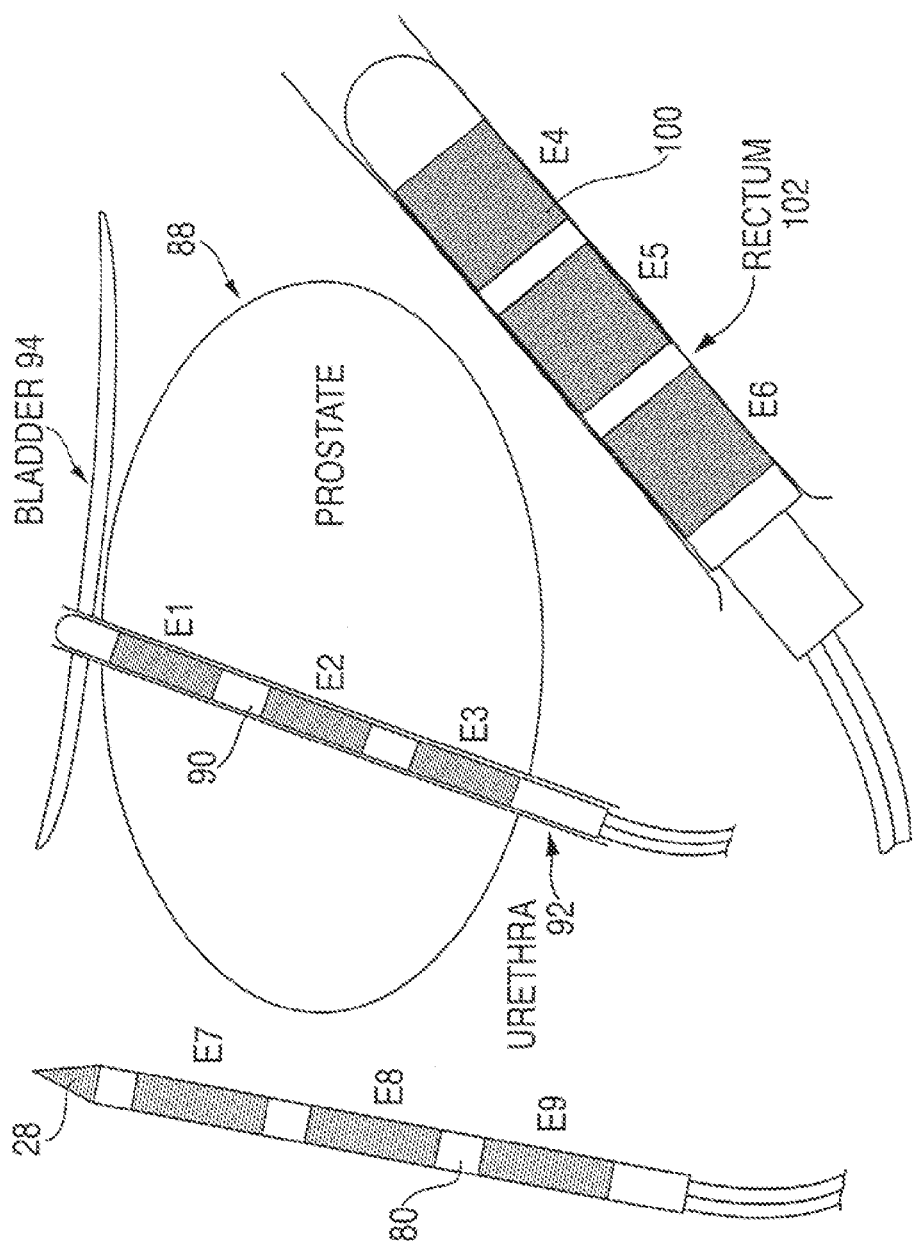
FIG. 8 is a schematic representation of a "Macro Prostate" treatment where the entire prostate gland is heated as to destroy the entire prostate gland while simultaneously protecting the rectal and urethra biologic structures via dynamically cooling of the electrodes.

FIG. 8 illustrates a macro method and apparatus for heating the entire prostate gland 88 in a male patient using dynamic and proportional current steering and three electrode shafts. A urethral electrode shaft 90, having three electrode hands E1, E2, E3, is designed and sized to be inserted into urethra 92 and have a diameter of from about 6 mm to about 8 mm, slightly larger than the diameter of a normal urethra or urethral opening. A rectal electrode shaft 100, having three electrode bands E4, E5, E6, is designed and sized to be inserted into rectum 102 and have a diameter of from about 2 cm to about 6 cm, slightly larger than the diameter of a normal rectum. By stretching the construct of urethra 92 and rectum 102, the smooth, conformal surfaces of electrode shaft 90, electrode bands E1, E2, E3, electrode shaft 100, and electrode bands E4, B5, E6 are provided with a highly efficient means of electrical conductivity so as to allow current to flow between urethra electrode hands E1, E2, E3 and rectal electrode bands E4, E5, E6. Electrode shafts 90 and 100 are dynamically cooled so as not to damage healthy tissue of the urethra or rectum. Optionally there may be an inflatable annular ring or other structure to stabilize electrode shaft 100 within rectum 102.

A third electrode shaft 80 with electrode bands E7, E8, E9 is inserted from the bottom into the patient's body at a position out of the plane of electrode shafts 90 and 100. Electrode shaft 80 has a diameter of from about 1 mm to about 2.5 mm. The length of each of electrodes 80, 90, and 100 wall be determined by the surgeon according to the application. Each of electrode shafts 80, 90, and 100 can be rotated or slid Longitudinally to facilitate hyperthermia capture of the entire prostate gland. Electrode shaft 90 should be positioned so that electrode hand E1 remains within prostate 88 and away from bladder 94 so that there is not any damage to bladder 94.

Figure 9:
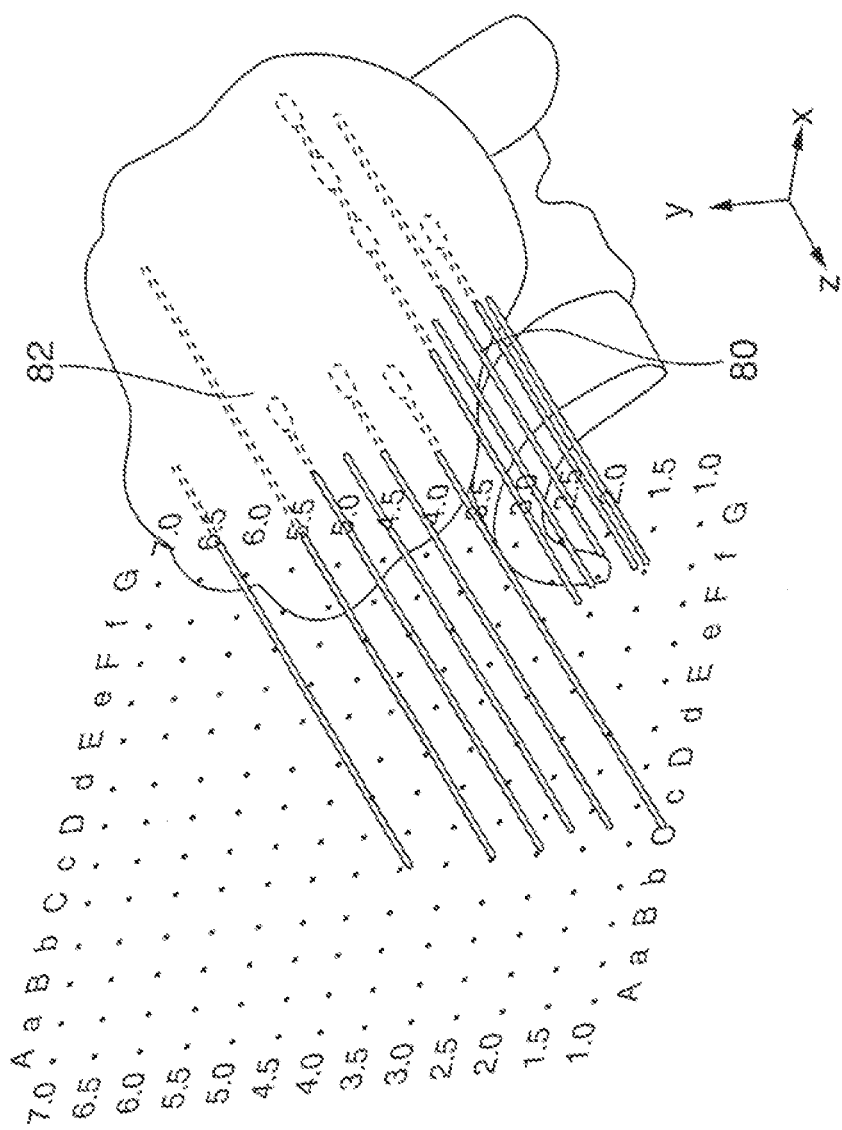
FIG. 9 is a schematic representation of shafts that have been inserted into a mass to sequentially map and treat the mass.

FIG. 9 is a schematic representation of a mapping and treatment procedure where shafts 80 have been inserted into a mass 82 to map and treat mass 82. Shafts 80, which can be biopsy probes, needles, or other longitudinally extending members that sense parameters or release chemicals, are typically inserted in predetermined patterns and orientations using a grid plate or template so that the surgeon can determine the extent, that is, the width, depth, length, and shape, of mass 82, optionally in concert with the appropriate imaging and scanning devices. When the extent of a mass is determined, the shafts 80 can be withdrawn and three or more electrode shafts comprising three platinum bands as electrodes (not shown here) can be inserted to dynamically and proportionally steer current vectors through the mass, as described above. Alternatively, some or all of shafts 80 may be a combination of biopsy probe or needle and an electrode shaft so that once appropriate imaging and scanning maps and precisely locates a cancerous or benign mass, the mass can be treated using voltages and currents as represented in the present invention stated herein as an "all in one procedure" which is advantageous for the patient. Thus, in accordance with an embodiment of the invention, three or more of shafts 80 comprise two or more electrode bands so that current vectors can be dynamically and proportionally steered to destroy the mass or masses discovered during the mapping procedure.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot foe used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for treating a mass within a patient's body, which comprises:
   three or more electrode shafts that define an area, each shaft having at least two electrode bands positioned along the shaft;
   a processor configured to generate instructive signals that are DC arbitrary waveforms or AC arbitrary waveforms of a frequency of up to about 1 KHz; and
   an amplifier array configured to receive instructive signals from the processor and to deliver signals to the electrode bands,
   wherein the processor is configured to control the amplifier array in such a way as to proportionately vary the voltage amplitude of signals to the electrode bands to dynamically steer and focus ionic current vectors to create and steer a hot zone anywhere in three dimensions within the area between the electrode shafts, without moving the electrodes, to resistively heat the mass to ensure destruction of all malignant or benign cells.

2. The system of claim 1, wherein the processor contains pre-programmed protocols to permit a medically trained operator to select a particular protocol for treating a mass.

3. The system of claim 1, wherein each electrode shaft has two or more platinum bands or contact points as electrode bands.

4. The system of claim 1, wherein each electrode shaft has an insertion diameter of from about 0.9 mm to about 5 mm.

5. The system of claim 1, wherein each electrode shaft has a distal tip with a dissolvable coating or substrate.

6. The system of claim 1, wherein each electrode shaft has one or more inflatable components that can be inflated to provide mechanical stability while surrounding a malignant or benign mass being treated.

7. The system of claim 1 which is suitable for treating malignant or benign masses which occur in a breast, liver, lungs, brain, pancreas, uterus, prostate, or ovary or elsewhere within a patient's body.

8. The system of claim 1, wherein each electrode shaft comprises a cooling system to dynamically cool the electrode bands during treatment.

9. The system of claim 1, wherein the materials and construction of the electrode shafts and electrode bands will be such that visual surface contrasts of the electrode shafts and the electrode bands can be differentiated by a medically trained operator using conventional ultrasound or other imaging equipment.

10. The system of claim 1, wherein all the ionic current vectors combine to generate controlled and focused hyperthermia.

11. The system of claim 1, which is configured to electronically steer the ionic current vectors to uniformly elevate areas of the mass to a temperature of from about 48° C. to about 50° C., until all malignant or benign cells within the mass are neutralized so that further abnormal cell growth cannot occur.

12. The system of claim 1, which further comprises a grid block, wherein three or more electrode shafts with electrode bands will be capable of being inserted into holes within the grid block while an ultrasound video is used simultaneously as a mechanical guide to surround the malignant or benign mass.

13. The system of claim 1, wherein each electrode shaft has at least one thermal sensor to provide feedback to the processor.

14. The system of claim 1, wherein the processor samples and analyzes thermal data from the thermal sensors and manages the amplifier-delivered energy by adjusting voltage amplitudes and pulse-widths of waveforms delivered to the electrode bands.

15. A system for treating a mass within a patient's body, which comprises:
three or more electrode shafts that define an area, each shaft having at least two electrode bands positioned along the shaft;
a processor configured to generate instructive signals that are DC arbitrary waveforms or AC arbitrary waveforms of frequency of up to about 1 KHz; and
an amplifier array configured to receive instructive signals from the processor and to deliver signals to the electrode bands,
wherein the processor is configured to control the amplifier array in such a way as to proportionally vary the voltage amplitude of signals to the electrode bands to dynamically steer and focus ionic current vectors to create and steer a hot zone anywhere in three dimensions within the area between the electrode shafts and around the perimeter of the mass using a fencing technique, without moving the electrodes, to destroy vasculature which feeds nutrients and blood supply to the mass by resistive heating.

16. The system of claim 15, wherein each electrode shaft has at least one thermal sensor to provide feedback to the processor.

17. A system for treating a malignant or benign mass within a patient's body which comprises three or more electrode shafts that define an area, each shaft having at least two electrode bands positioned along the shaft, a computer processor-controlled electronic amplifier array which is configured to deliver signals that are DC arbitrary waveforms or AC arbitrary waveforms of frequency of up to about 1 KHz to the electrode bands, wherein the computer-controlled processor is configured to control the amplifier array in such a way as to proportionately vary the voltage amplitude of signals to the electrode bands to dynamically steer and focus ionic current vectors to create and steer a hot zone anywhere in three dimensions within the area between the three or more electrode shafts, without moving the electrodes, and wherein the mass is resistively heated sufficiently to neutralize all abnormal cells within the mass while minimizing damage to surrounding healthy tissue.

\* \* \* \* \*